US00PP09685P

United States Patent [19]

Bevelander

[11] Patent Number: Plant 9,685

[45] Date of Patent: Nov. 5, 1996

[54] POINSETTIA PLANT NAMED 'MARBLESTAR'

[76] Inventor: Marinus J. Bevelander, Bankrasweg 6B, 1183 TP Amstelveen, Netherlands

[21] Appl. No.: 436,630

[22] Filed: May 8, 1995

[51] Int. Cl.[6] ..... A01H 5/00

[52] U.S. Cl. ..... Plt./86.1

[58] Field of Search ..... Plt./86.1

[56] References Cited

U.S. PATENT DOCUMENTS

P.P. 9,315 10/1995 Zerr ..... Plt./86.1

P.P. 9,316 10/1995 Zerr ..... Plt/86.1

*Primary Examiner*—James R. Feyrer

*Attorney, Agent, or Firm*—Foley & Lardner

[57] ABSTRACT

A distinct cultivar of poinsettia plant named Marblestar, characterized by the combined traits of salmon pink main bract color with irregular cream-white margins, medium to dark green foliage, compact to medium tall, bushy plant habit, medium early flowering response, and good color retention.

1 Drawing Sheet

The present invention relates to a new and distinct cultivar of poinsettia plant known by the cultivar named Marblestar, and botanically known as *Euphorbia pulcherrima.*

The new cultivar is a naturally occurring mutation of Peterstar, disclosed in U.S. Plant Pat. No. 8,259 and characterized by its bright red bract color, medium green foliage, compact habit, and good branching ability.

The new cultivar was discovered by the inventor Marinus J. Bevelander as a mutation among a group of stock plants of the parent cultivar Peterstar growing in a greenhouse in Rijssenhout, The Netherlands, in September 1993. One plant possessed a partly mutated involucre in which some of the single bracts were completely or partly pink colored, with most of these having white margins.

Cuttings were taken by the inventor in Rijssenhout from shoots evolving from the mutated branch of the parent plant, plant containing the pink bract color and white margins, and these cuttings were planted and grown out. The results were plants having bracts with large areas of salmon pink, and white margins. The plants having the salmon pink bracts with white margins were asexually propagated by the inventor and selected several times until the new cultivar having uniform and stable characteristics was obtained.

Horticultural examination initiated in 1994 and continuing thereafter has demonstrated that the combination of characteritics as herein disclosed for Marblestar are firmly fixed and are retained thrugh successive generations of asexual reproduction.

The following traits have been repeatedly observed and are determined to be basic characteristics of Marblestar which in combination distinguish this poinsettia as a new and distinct cultivar:

1. Intense salmon pink bracts with irregular cream-white margins.
2. Broad elliptically shaped bracts with somewhat rugose texture.
3. Medium to dark green foliage.
4. Compact to medium tall, bushy plant habit.
5. Medium early flowering response.
6. Good stability of bract color upon maturation.

Marblestar has not been observed under all possible environmental conditions. The phenotype may vary significantly with variations in environment such as temperature, light intensity, and daylength without, however, any variance in genotype. The following observations, measurements, and comparisons describe plants grown in Aalsmeer, The Netherlands, under greenhouse conditions which approximate those generally used in commercial practice.

Of the many commercial cultivars known to the inventor, the most similar in comparison to Marblestar are the parent cultivar Peterstar and the cultivar Beckmann's Altrosa, also a mutation of Peterstar and disclosed in a pending application. In comparison to Peterstar, Marblestar has salmon pink and white variegated bract color, more intense green foliage, and a somewhat slower and less vigorous growth habit.

In comparison to Beckmann's Altrosa, the main bract color of Marblestar is a slightly different shade of pink, the bracts of Marblestar have an irregularly shaped cream-white margin, and the foliage of Marblestar is darker green in color.

The accompanying color photographic drawing comprises a top perspective view showing the inflorescence and foliage of a typical plant of Marblestar, with colors being as true as possible with illustrations of this type.

In the following description, color references are made to the Royal Horticultural Society Colour Chart. The color values were determined indoors in a north light. The plants described were grown in Aalsmeer, The Netherlands, in 1994. Observations and measurements were taken at the beginning of flowering.

Classification:

*Botanical.*—*Euphorbia pulcherrima.*

*Commercial.*—Poinsettia, cv Marblestar.

Origin: Naturally occurring mutation of 'Peterstar'.

Plant description

*Form.*—Bushy, well branched.

*Growth habit.*—Compact to medium tall, less vigorously growing than Peterstar, when grown in 13 cm pots; when plant height is 30–35 cm (above soil line) 4–6 branches are developed. Branched plants of Marblestar are usually about 85% the height of Peterstar. Internode length of Marblestar is approximately 2 cm, slightly less on average than Peterstar.

*Blooming season.*—Under natural short day conditions in late November, about 9 weeks of response time; saleable when cyathias open or few days earlier.

*Foliage.*—Size: Leafblade is 13 cm in length, petiole is 6 cm. Color: Mature foliage upper surface between 137A and 139A; under surface 137C; veins are light green. Leaf petiole: Upper and lower sides are light green, with slight infusion of anthocyanin producing a light brown color. Shape: Ovate to elliptical, slight lobate, rounded base and acuminated tip, sinus between lobes rounded. Texture: Slightly rugose, weak veins. Edge of margin: Slightly undulated, entire, apart from the lobes. Disease resistance: Not observed to be particularly resistant or susceptible to disease.

Flowering description:

*Cyathias.*—Color and size: Light green, top salmon, diameter about 5 mm. Borne: 10–15 in a narrow cluster. Retention: Good.

*Bracts.*—Shape: Ovate to broad elliptical, slightly folded, rounded base and pointed tip. Texture: Surface rugose, light green or light red midribs; light green to almost white veining on under surface.

*Color.*—Main part of upper surface dark pink to pink, 48A–B, with lighter pink spots between 48 D and 51 D thereby creating a marbled effect; margin is cream-white approximately 159A and irregularly shaped; undersurface 48C/D with no marbling, and cream white margin 159 A light green to greenish white veins.

*Size.*—Largest bract is approximately 11.5 cm in length and 7 cm in width.

Aspect.—Borne somewhat upright, slightly reflexed.

Petiole.—1–2 cm in length, light red to brownish pink, about 39A.

Reproductive organs:

*Glands, nectar cups.*—Orange-yellow.

*Stamens.*—Light red, turning brown (abortive).

*Pollen.*—Very little, yellow.

*Styles.*—Whitish style and pink 6-lobed stigma.

*Ovaries.*—Triangular, 3-celled, 3 ovules.

*Fecundity.*—Male sterile, female almost sterile; hardly ever sets seeds even after pollination.

Disease resistance:

Marblestar appears to have average disease resistance, although young plants appear to be somewhat susceptible to Botrytis.

It is claimed:

1. A new and distinct poinsettia plant named Marblestar, as illustrated and described.

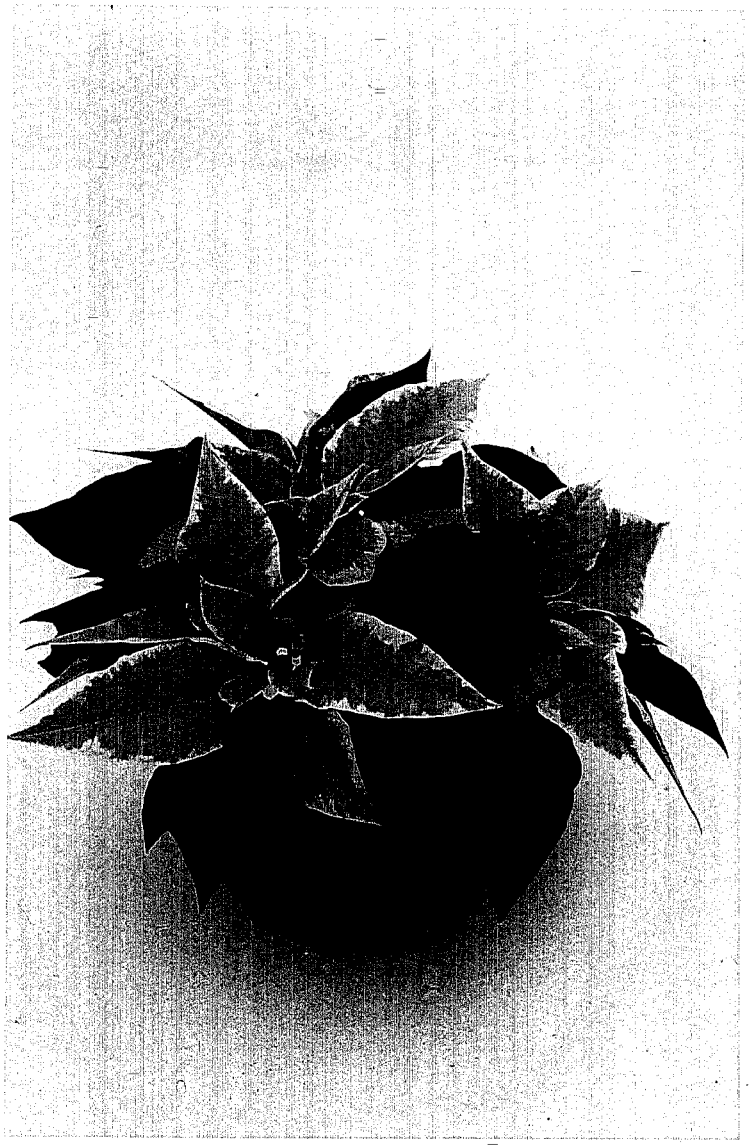

* * * * *